(12) United States Patent
Törnsten et al.

(10) Patent No.: US 10,835,684 B2
(45) Date of Patent: Nov. 17, 2020

(54) TRACK-INDEXED SYRINGE (71) Applicant: NESTLÉ SKIN HEALTH S.A, Lausanne (CH)

(72) Inventors: Jonas Törnsten, Uppsala (SE); Max Blomqvist, Uppsala (SE)

(73) Assignee: NESTLÉ SKIN HEALTH S.A., Lausanne (CH)

( * ) Notice: Subject to any disclaimer, the term of this patent is extended or adjusted under 35 U.S.C. 154(b) by 11 days.

(21) Appl. No.: 15/560,593

(22) PCT Filed: Mar. 24, 2016

(86) PCT No.: PCT/EP2016/056559
§ 371 (c)(1),
(2) Date: Sep. 22, 2017

(87) PCT Pub. No.: WO2016/151091
PCT Pub. Date: Sep. 29, 2016

(65) Prior Publication Data
US 2018/0085529 A1    Mar. 29, 2018

(30) Foreign Application Priority Data
Mar. 25, 2015   (EP) ..................................... 15160799

(51) Int. Cl.
*A61M 5/315*    (2006.01)
(52) U.S. Cl.
CPC .... *A61M 5/31573* (2013.01); *A61M 5/31595* (2013.01); *A61M 2205/581* (2013.01); *A61M 2205/582* (2013.01)
(58) Field of Classification Search
CPC .......... A61M 5/31573; A61M 5/31595; A61M 2205/581; A61M 2205/582
See application file for complete search history.

(56) References Cited

U.S. PATENT DOCUMENTS 2,474,496 A * 6/1949 Rayman ............ A61M 5/31555
604/210
4,466,426 A * 8/1984 Blackman ........... A61M 5/3158
600/5

(Continued)

FOREIGN PATENT DOCUMENTS

EP    2 821 089 A1    1/2015
FR      364 517 A      8/1906

(Continued)

OTHER PUBLICATIONS

International Search Report (PCT/ISA/210) dated Jul. 14, 2016, by the European Patent Office as the International Searching Authority for International Application No. PCT/EP2016/056559.

(Continued)

*Primary Examiner* — Rebecca E Eisenberg
*Assistant Examiner* — John A Doubrava
(74) *Attorney, Agent, or Firm* — Foley & Lardner LLP; Sunit Talapatra (57) ABSTRACT

A syringe including a barrel, a plunger moveably arranged within the barrel and a plunger rod for driving the plunger, and an engagement member arranged at the barrel to engage with a grooved surface on the plunger rod. This will create feedback given to a user as the plunger rod is moved relative to the barrel for driving the plunger within the barrel. The barrel and the engagement member are arranged relative to each other such that the engagement member, due to the engagement with the grooved surface of the plunger rod, will move solely in a direction generally perpendicular to a longitudinal direction of the plunger rod as the plunger rod is moved relative to the barrel.

12 Claims, 5 Drawing Sheets

(56) References Cited

U.S. PATENT DOCUMENTS

| | | | | |
|---|---|---|---|---|
| 4,826,483 A | * | 5/1989 | Molnar, IV | A61M 5/5013 604/110 |
| 7,611,495 B1 | * | 11/2009 | Gianturco | A61M 5/31501 604/207 |
| 2003/0225358 A1 | | 12/2003 | Berman et al. | |
| 2007/0265579 A1 | | 11/2007 | Kleyman et al. | |
| 2013/0317448 A1 | * | 11/2013 | Hourmand | A61M 5/2033 604/197 |
| 2015/0045740 A1 | | 2/2015 | Kojima et al. | |

FOREIGN PATENT DOCUMENTS

| | | |
|---|---|---|
| FR | 1 054 173 A | 2/1954 |
| GB | 1 225 495 A | 3/1971 |
| WO | WO 2008/057976 A2 | 5/2008 |
| WO | WO 2013/161434 A1 | 10/2013 |

OTHER PUBLICATIONS

Written Opinion (PCT/ISA/237) dated Jul. 14, 2016, by the European Patent Office as the International Searching Authority for International Application No. PCT/EP2016/056559.

* cited by examiner

TRACK-INDEXED SYRINGE

FIELD OF THE INVENTION

The present invention relates to syringes, and more particularly to a syringe that is able to provide a user with feedback during use.

BACKGROUND OF THE INVENTION

When a user of a medical syringe administers a substance, it is common, in particular within certain areas of treatment, to distribute the total volume carried by the syringe over an area. Some examples of such areas of treatment are dermatology, plastic surgery, cosmetic surgery, and odontology. The distribution is for instance done by inserting the needle of the syringe just beneath and approximately in parallel with the skin surface and then administering the substance while withdrawing the needle. Another way is to administer the substance at several anatomic locations within a limited area, i.e. to administer a fraction of the total volume at each location. In both these, and other, methods of distributing the substance it is an advantage if the syringe is provided with some kind of dosing aid, which aids the user in knowing how large fraction of the total volume of the substance is administered at each location or per time unit. Conventionally, the syringe barrel is provided with a gradation scale, and the user observes the position of the plunger along the scale. However, the scale is difficult to see and might sometimes be partly or fully covered by a sticker, or the like, and the syringe is at times held at an angle where the scale is hidden. Another practical problem with gradation scales provided on the syringe barrel is that sometimes very small amounts of a substance shall be provided which requires correspondingly small movements of the plunger in the barrel which movements can be hard to detect by a user. Further, a main problem with the use of a gradation scale as such is the fact that a user has to observe it during injection which means that a distraction of attention arises when the user has to look at the gradation scale every now and then instead of focusing on the course of events at the treatment area. Mechanic or electronic injectors providing an accurate dosing have been used, but they are more expensive and heavier than syringes and many users prefer to hold the injection device in the way that a conventional syringe is held. Further, most injectors do not allow a user to perform needle aspiration prior to injection of the medicament. This is a serious drawback since it does not allow a user to realize that injection has been done in a blood vessel. Also, this prevents the use of substances that need to be drawn up into the barrel of the syringe from a reservoir containing the substance prior to injection.

An effort to provide a syringe with a dosing aid is disclosed in WO 2008/057976, where an engagement member is provided on the finger grip and engages with a structure of the plunger rod.

SUMMARY OF THE INVENTION

It would be advantageous to provide a syringe with user friendly means that informs and provides feedback to a user about the injected amount or an injection rate and which also has a simple construction.

To better address at least some of these concerns, in a first aspect of the invention it is presented a syringe comprising a barrel and a plunger which is moveably arranged within the barrel. The syringe further comprises a plunger rod intended for driving the plunger in a direction parallel to a longitudinal direction of the plunger rod for expelling or drawing up of a substance. Further, an engagement member is arranged at the barrel to engage with a grooved surface provided on the plunger rod such that feedback is given to a user as the plunger is moved relative to the barrel for driving the plunger. The barrel and the engagement member are arranged relative to each other such that the engagement member, due to the engagement and interaction with the grooved surface of the plunger rod, will move solely in a direction generally perpendicular to a longitudinal direction of the plunger rod as the plunger rod is moved relative to the barrel for driving the plunger. This construction will provide for an improved dosing accuracy. With the solution presented in WO-2008/057976 the engagement member consists of a flat member lying on top of the finger grip, see e.g. FIGS. 3 and 4 in that prior art document. A major drawback with that prior art solution has been identified where a user intends to administer e.g. botulinum toxin. Typically, botulinum toxin has to be drawn up into the barrel of an empty syringe from a reservoir prior to injection. When this is done with a syringe as described in WO-2008/057976, at the end of the draw up operation, there is a high likelihood that the flat engagement member will be situated in a position where it is slightly bent upwards resting on a ridge of the grooved surface of the plunger rod. The engagement member of the prior art will thus be biased in the wrong direction. Normally, one click from the engagement member represents a certain dose of the substance in the barrel corresponding to the distance between two adjacent ridges of the grooved surface of the plunger rod. However, the fact that the starting position of the engagement member of WO-2008/057976 will be one where it is bent slightly upwards, the plunger rod will have to travel much farther than what was initially intended before the first click-sound is generated by the engagement member. The engagement member will in this case have to move first from its position bent slightly upwards towards a position where it is horizontal and thereafter towards a position where it is bent slightly downwards before the first click-sound will be generated. Continued movement will of course cause repeated click-sounds caused by the interaction between the engagement member and the grooved surface of the plunger rod having an intended dose. However, tests have proven that a first dose with such prior art constructions can be up to three time larger than actually intended and such overdosing can in certain situations be catastrophic for patients causing e.g. unintended muscle paralysis. It should also be noted, that these continued click-sounds are generated with the engagement member of that prior art solution positioned in a position where it at all times is more or less bent downwardly. This means that during injection when the engagement member passes over a ridge of the grooved surface of the moving plunger rod and hits an adjacent ridge, thus creating the click-sound, it will most likely never assume a horizontal position. Therefore, another situation where a too large dosis can be expelled by a syringe according to that prior art solution is when the click function is switched-off during e.g. aspiration or draw-up of a substance or if it for some reason is switched-off during treatment. If the click function thereafter is resumed again, the engagement member will be introduced to the grooved surface in a neutral position perpendicular to the longitudinal direction of the plunger rod and will therefore require the plunger rod to travel farther the initially intended before a first click sound will be generated. The same applies to a situation where a pre-filled syringe having an engagement member as described in that prior art is used. In this case the engagement member will be positioned in a position perpendicular to the longitudinal direction of the plunger rod and will also require the plunger rod to travel farther the initially intended before a first click sound will be generated. With the solution of the present invention, where the engagement member is arranged to only travel in a direction perpendicular to the longitudinal direction of the plunger rod, this drawback is avoided. Similar to WO-2008/057976, in the present invention the distance between two ridges of the grooved surface of the plunger rod corresponds to a certain dose and is represented by one click during use. In contrast to that prior art solution, with a syringe according to the present invention the first click after the substance has been drawn up represents no more than one dose. This since the engagement member of the present invention will never require any initial travel to relieve a bias in the wrong direction such as it is required by the prior art solutions. This since the engagement member of the present invention will never, as in the prior art solution, merely travel with the grooved surface of the plunger rod towards a position where the click-sound generating movement of the engagement member is even initiated. Instead, the engagement member of the present invention always reciprocates between an outer and an inner end position irrespective of the direction in which the plunger rod is moved or has previously been moved, e.g. after draw up of a substance. Hence, an overdosing as it is risked by the prior art solutions is not possible with the present invention.

In accordance with an embodiment of the syringe, the engagement member is arranged within the barrel.

In accordance with an embodiment of the syringe, the engagement member is arranged at the barrel immovable in a direction parallel to the longitudinal direction of the plunger rod. By avoiding any play or similar between the barrel and the engagement member the dosing accuracy is improved.

In accordance with an embodiment of the syringe, the immovable arrangement of the engagement member at the barrel is achieved by a tight fit. A tight fit between the two parts is a simple yet reliable way of arranging them immovably to each other since no separate attaching members or means are required.

In accordance with an embodiment of the syringe, the immovable arrangement of the engagement member at the barrel is achieved by a snap locking. A snap-lock is another simple and reliable solution which is easy to manufacture and provides for simple assembly of the syringe.

In accordance with an embodiment of the syringe, the immovable arrangement of the engagement member at the barrel is achieved by a cap arranged at the barrel. A separate cap can also be provided to secure the engagement member to the barrel.

In accordance with an embodiment of the syringe, the engagement member comprises a main part having a circular or semi-circular shape and a protruding element protruding from the main part for engaging the grooved surface of the plunger rod. A circular or semi-circular engagement member encircling the plunger rod at least partly and having an inwardly protruding element that engages the grooved surface of the plunger rod is simple to arranged within a barrel which is typically circular in cross-section and it also easy to provide such engagement member with a suitable prestress in a direction perpendicular to the longitudinal direction of the plunger rod such that the protruding element will at all time abut the grooved surface of the plunger rod.

In accordance with an embodiment of the syringe, the engagement member comprises a main part being generally plate shaped and a protruding element protruding from the main part for engaging the grooved surface of the plunger rod. A plate shaped main part having a protrusion thereon provides for a very simple manufacturing and assembly.

In accordance with an embodiment of the syringe, the protruding element is connected to the main part along an edge of the protruding element. This edge extends generally in parallel with the longitudinal direction of the plunger rod. This arrangement will provide a high degree of rigidity such that any deflection of the protruding element in a direction parallel to the longitudinal direction of the plunger rod can be avoided completely or at least to a large extent.

In accordance with an embodiment of the syringe, the protruding element is folded from the main part of the engagement member along the edge. By folding the protruding element from the main part, a strong and reliable construction is obtained.

In accordance with an embodiment of the syringe, the protruding element is punched out from the main part of the engagement member.

In accordance with an embodiment of the syringe, the engagement member comprises a main part having a semi-circular shape and a protruding element, wherein the protruding element is arranged as an extension of the main part and having a narrower bending radius than said main part such that an end of the protruding element engages the grooved surface of the plunger rod. By curving the protruding element with a radius that is sufficiently narrow, the protruding member will be directed towards and engaging with the grooved surface of the plunger rod.

In accordance with an embodiment of the syringe, the engagement member comprises a main part having a semi-circular shape and a protruding element for engaging the grooved surface of the plunger rod, wherein the protruding element is arranged as an extension of the main part by folding along an edge generally parallel to the longitudinal direction of the plunger rod.

In accordance with an embodiment of the syringe, the engagement member is arranged in a compartment of the barrel being generally shaped as an annulus, wherein the plunger rod extends through the inner circle of the annulus and wherein the engagement member can engage the grooved surface of the plunger rod through an opening in the compartment.

In accordance with an embodiment of the syringe, the plate shaped main part of the engagement member is attached to the barrel along two edges of the plate shaped main part. By attaching the plate shaped member along two, possibly opposed, edges the main part can bias the protruding member towards the grooved surface of the plunger rod. Further, this will allow the plate shaped main part to act as an acoustic membrane enhancing the click sound of the syringe.

In accordance with an embodiment of the syringe, an end portion of the engagement member engaging with the grooved surface of the plunger rod has a tapering such that feedback is given to a user irrespective of the moving direction of the plunger rod. This is an important aspect since it is often desirable to have the click sound also during aspiration and draw up of substances. Also, this provides the possibility of providing a syringe that always assumes a given start position. For example, when a substance has been drawn up into the barrel of the syringe and the user releases the grip on the plunger rod, the tapered end portion can cause the plunger rod to move slightly until the tapered end reaches a bottom of the of the grooved surface of the plunger rod. This of course also requires that a sufficient preload is placed on the protruding member from e.g. the main part of the engagement member. This action can be further alleviated by choosing a suitable geometry and surface material of the grooved surface of the plunger rod.

These and other aspects and advantages of the invention will be apparent from and elucidated with reference to the embodiments described hereinafter.

BRIEF DESCRIPTION OF THE DRAWINGS

The invention will now be described in more detail and with reference to the appended drawings in which.

DESCRIPTION OF PREFERRED EMBODIMENTS

Figure 1:
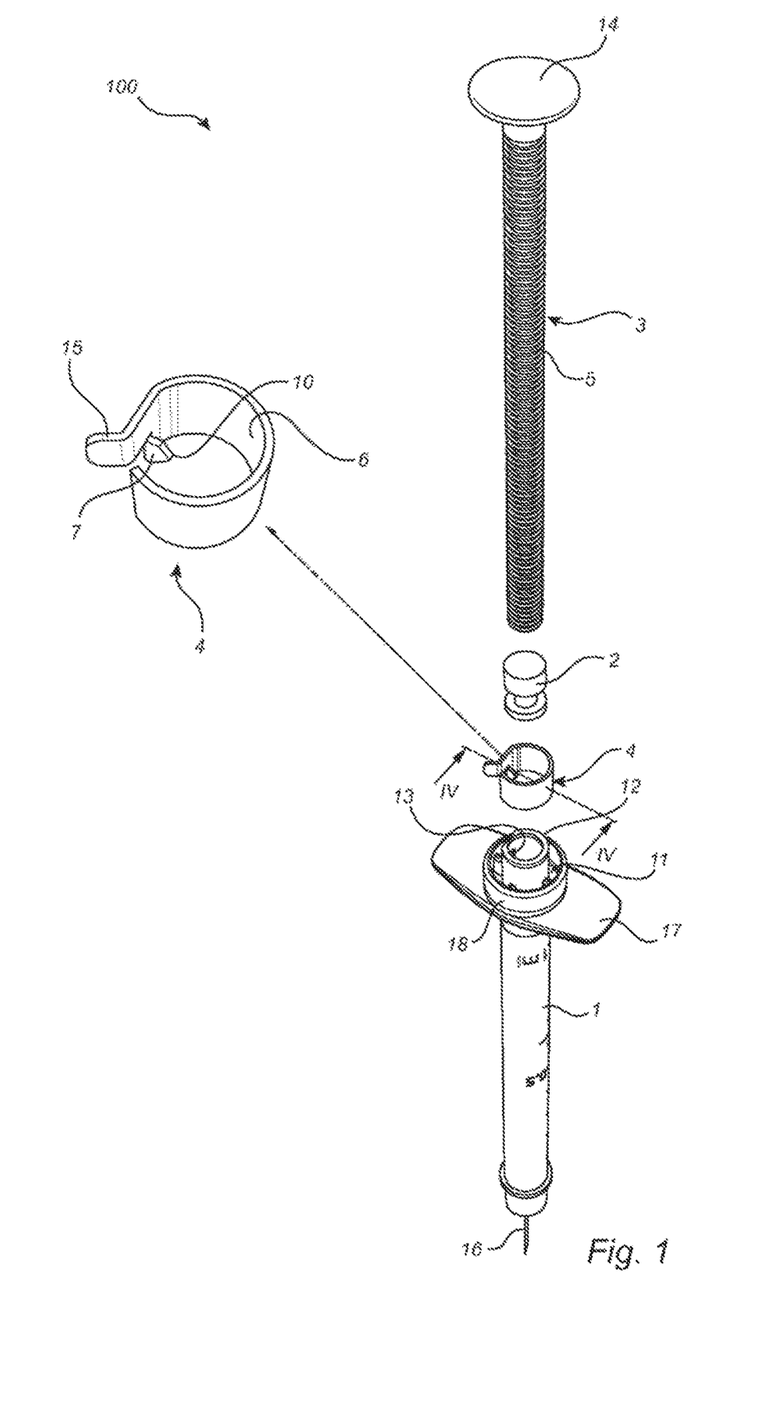
FIG. 1 is a perspective view of a first embodiment of a syringe according to the present invention.

An embodiment of the syringe 100, as most schematically illustrated in FIG. 1, comprises a barrel 1, a plunger 2 and a plunger rod 3 arranged to drive the plunger 2 during use of the syringe 100 and is provided with a thumb plate 14 for activation of the plunger rod 3. The plunger rod 3 can be attached to the plunger 2 by any suitable means as would be obvious to the skilled person. A threaded connection would for example be suitable since it allows for the plunger 2 to be moved in both directions, i.e. pushed and pulled through the barrel 1, which is not always possible with other connecting means. The syringe 100 further comprises a needle 16 and the barrel 1 can be provided with a finger grip 17. The plunger rod 3 is provided with a grooved outer surface 5 having a plurality of ridges and valleys provided in an alternating manner along a length of the plunger rod 3. This can be achieved by providing the plunger rod 3 with a large number of narrow grooves, defined by narrow flanges. Different shapes of the flanges can be imagined and chosen depending on the requirements. For example, they can protrude from the plunger rod perpendicularly to a longitudinal axis of the plunger rod. Another possibility is to provide such flanges having a wedge shape that is symmetrical about a plane that extends perpendicularly to a longitudinal axis of the plunger rod through the outer tip of the flange. Another possibility is a non-symmetrical wedge shape. Yet another possible shape is best disclosed in FIGS. 4a and 4b and can be described to correspond to a plurality of frustums stacked on top of each other. The pitch of the flanges, i.e. the centre distance between two adjacent flanges, is typically between 0.1 and 3 mm. The pitch is typically chosen depending on the substance to be injected and the size, i.e. the diameter, of the barrel 1 of the syringe 100. A narrow barrel 1 means that a smaller amount is expelled from the syringe 100 for a given travel of the plunger 2 and accordingly a larger pitch of the flanges has to be used to represent a certain amount of injected substance. Further, the plunger rod 3 could be carried out as a hollow rod. The plunger rod 3 could be manufactured by injection moulding and if the plunger rod 3 is made solid, cooling of the product would be rather time consuming in order to avoid problems with shrinkage which in turn would cause tolerance problems of the flanges, i.e. varying distances between flanges and varying protrusion of the flanges. Such tolerance variations are of course unwanted and often not tolerable. Therefore, the plunger rod 3 could be made hollow which saves material and remedies the cooling and tolerance problems. The syringe 100 further comprises a compartment 11 generally defined by an outer cylindrical element 18 and an inner cylindrical element 12 and an engagement member 4 arranged within said compartment 11. Of course, other shapes of the compartment 11 are imaginable, e.g. square, elliptic etc. In the embodiment shown in FIG. 1, the engagement member 4 comprises a semi-circular element 6, a protruding element 7 and an adjusting member 15. The engagement member 4 is arranged within the compartment 11 in such manner that the protruding element 7 reaches through an opening 13 in the inner cylindrical element 12 and engages with the grooved surface 5 of the plunger rod 3. Typically, the engagement member 4 is retained within compartment 11 such that it can move to a certain degree in a direction perpendicular to the longitudinal direction of the plunger rod 3 but is prevented from any movement in a direction parallel to the longitudinal direction of the plunger rod 3. This retention can be provided in a number of ways. For example a cap 19, as is shown in FIG. 5, can be provided such that the engagement member 4 is free to move within compartment 11 in a direction perpendicular to the longitudinal direction of the plunger rod 3 but is prevented from any movement in a direction parallel to the longitudinal direction of the plunger rod 3. Other suitable means are slots into which the engagement member 4 can be inserted with a tight or press fit or snap-lock means that will lock the engagement member 4 in place. When the user is administering the medical substance, and thus pushes the plunger rod 3 further into the barrel 1, a sound is generated by the flanges passing the engagement member 4, causing the engagement member 4 to move in a direction perpendicular to the longitudinal direction of the plunger rod 3 which gives feedback to the user in the form of a click-sound and possibly also in the form of a tactile feedback. It is easy for the user to learn to associate the click-sound with the amount of medical substance that is administered, and also to associate the sound with a certain injection rate, thereby allowing the user to accurately dose the substance and distribute it as desired. The motion pattern of the engagement member 4 of the present invention has a major advantage in that one click-sound always represents the initially intended dose corresponding to one click. In some of the prior art solutions, there is a problem with engagement members that during aspiration or draw up of a substance will be biased in an opposite direction and will during injection of a first dose require the plunger rod to travel much farther than initially intended for one click before the first click-sound is generated. It has been shown in tests that the first dose in such prior art syringes can be up to three times larger than intended. Such overdosing is of course highly unwanted and can in certain cases have devastating effects. With the solution of the present invention, common to all embodiments of this patent application, the engagement member 4 always reciprocates back and forth between two given turning points irrespective of the direction in which the plunger rod 3 is driving the plunger 2 and no biasing in a wrong direction of the engagement member 4 is done, instead the protruding element 7 of the engagement member 4 always slides over the grooved surface 5 of the plunger rod 3 as the plunger rod 3 moves.

Figures 4A, 4B:
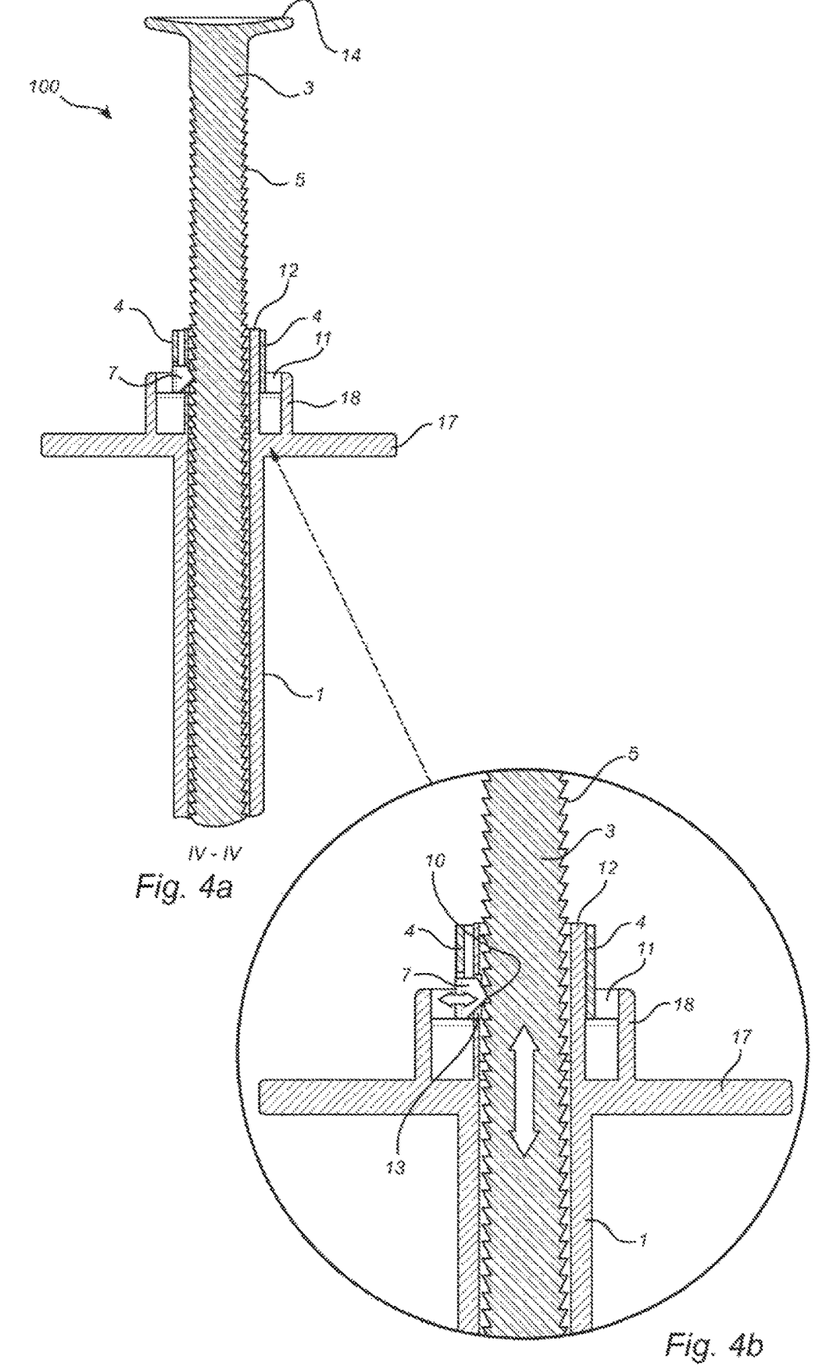
FIGS. 4a and 4b are cross-sectional views of a part of the syringe of FIG. 1.
Figure 5:
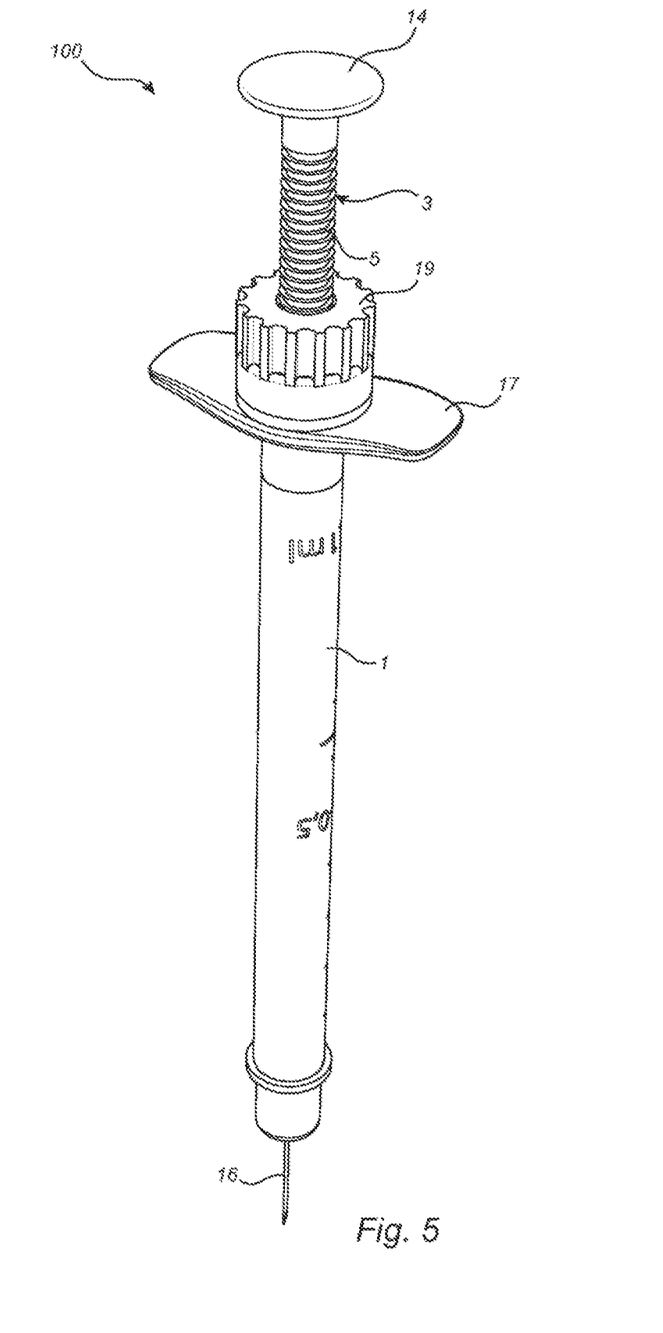
FIG. 5 is a perspective view of an embodiment of the syringe according to the present invention.

This is probably best shown in FIGS. 4a and 4b. This stands in sharp contrast to the mentioned prior art solution where the engagement member during a first part of a first dose merely rests on the grooved surface of the plunger rod and travels with it until it eventually reaches a position where the sliding movement of the engagement member and the actual click-function is initiated. In the embodiment shown in FIG. 1, the protruding element 7 of the engagement member 4 is folded from the main part 6. The engagement member 4 is typically made from metal having a thickness of ~0.03-0.5 mm. The height of the protruding element 7, i.e. the extension in a direction parallel to the longitudinal direction of the plunger rod 3, is chosen to be large enough to avoid that the protruding element 7 is bent in a direction parallel to the longitudinal axis of plunger rod 3, during use. Instead the moving of plunger rod 3 and the interaction between the grooved surface 5 and the protruding element 7 should only bring about a movement of the protruding element 7, and thus the whole engagement member 4, in a direction perpendicular to the longitudinal axis of plunger rod 3. Typically, the height of the protruding element 7 would lie between 1-10 mm. To this end, it could also be suitable to provide the end portion 10 with a tapering. A tapering of the end portion 10 can, in combination with a suitable preload of the main part 6 acting as a spring forcing the protruding element 7 against the grooved surface 5, also have the effect that when a user releases the force exerted on the plunger rod 3, during for example draw up of a substance, the plunger rod 3 will assume a position in which the tapered end portion 10 rests at the bottom between two ridges of the grooved surface 5. This could be especially interesting after draw up of a substance into barrel 1 since the dose of the first click in such case will be neither larger, nor smaller than initially intended. In any case, the pre-stress of main part 6 shall be large enough to make sure that the protruding element 7 always rests against the grooved surface 5 such that a click-sound is always generated when the plunger rod is moved. In the embodiment shown in FIG. 1, the click-function can be switched off by pressing adjusting member 15 in either direction, thus causing engagement member 4 to rotate within compartment 11. This will have the effect that protruding element 7 leaves the opening 13 and will thus no longer be in contact with the grooved surface 5.

Figure 2:
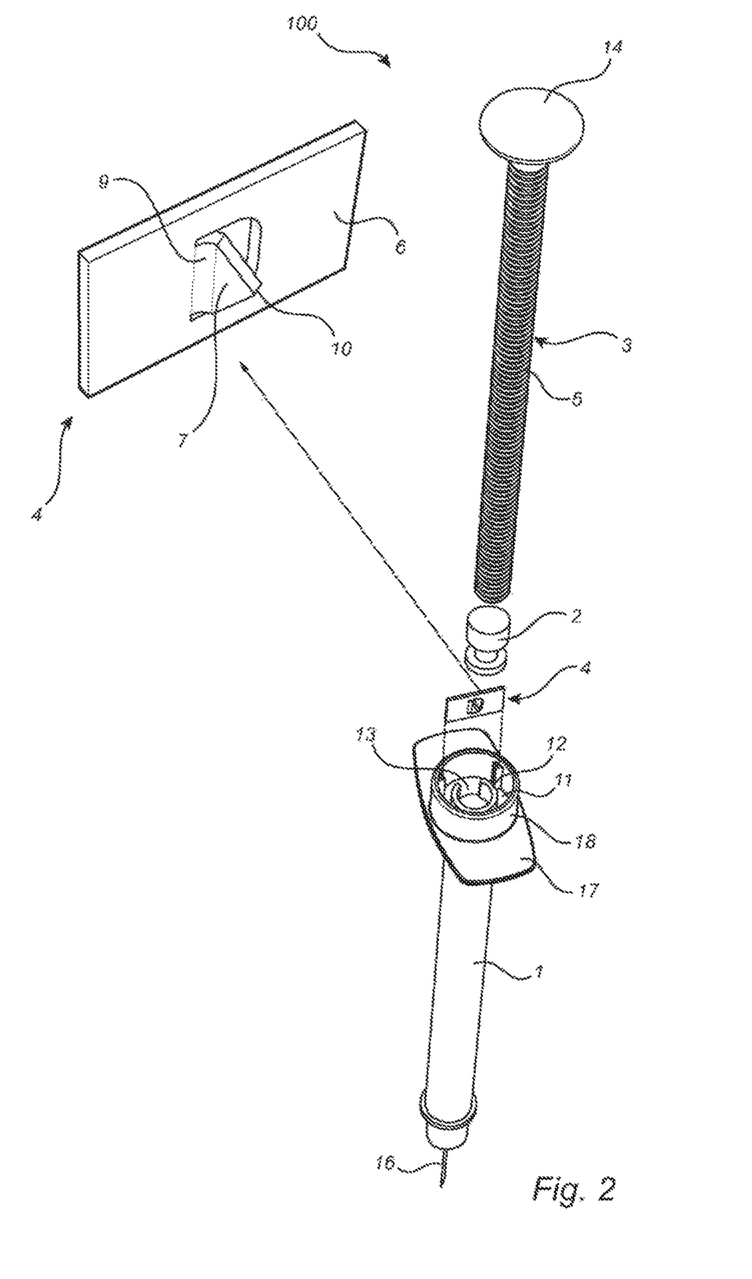
FIG. 2 is a perspective view of a second embodiment of a syringe according to the present invention.

In the embodiment shown in FIG. 2, the engagement member 4 is provided in the form of a plate shaped member having a main part 6 and a protruding element 7 folded out from the main part 6. Regarding the thickness of the engagement member 4 and the height of protruding element 7, the same applies as described in connection with FIG. 1. Of course, there are other suitable ways in which the protruding element 7 can be achieved. For example attaching it by welding or gluing; providing a welding spark on the surface of the main part 6; attaching a sufficiently stiff dowel or pin to the main part 6 etc. The engagement member 4 of FIG. 2 can be attached within the compartment 11 by means of slots arranged within the compartment 11 (shown in FIG. 2 but without reference numerals) that are either narrow enough to provide a tight or press fit with two opposing edges of the plate shaped engagement member 4 or the slots may be provided with snap-locks locking the engagement member 4 in place. A tight or press fit or snap-lock both have the advantage of being simple and allowing for cheap manufacture. Other means such as gluing, heat welding or the use of separate attachment means are of course also imaginable. The main thing is that the engagement member 4 is prevented from moving in a direction parallel with the longitudinal direction of the plunger rod 3. This of course applies for all embodiments of the present invention.

Figure 3:
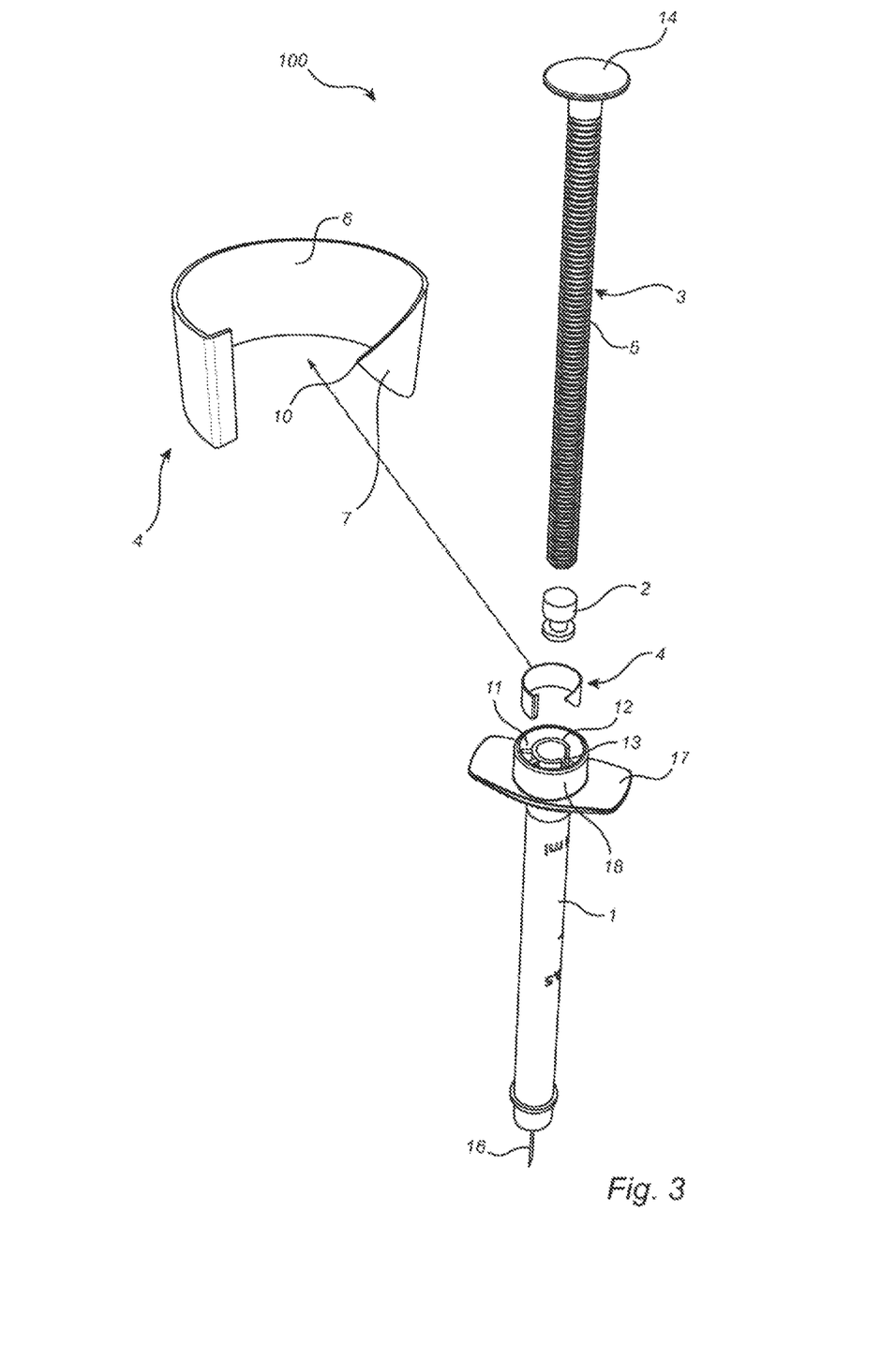
FIG. 3 is a perspective view of a third embodiment of a syringe according to the present invention.

In the embodiment shown in FIG. 3, the engagement member 4 is provided in the form of a continuous semi-circular element. Instead of being folded out from the main part 6, the protruding element 7 in this embodiment is created as a continuation of the main part 6 but having a narrower bending radius such that end portion 10 will abut the grooved surface 5 of the plunger rod 3. It should be noted that the protruding element 7 does not have to be bent as far as pointing in a direction of a radius of the plunger rod 3; it is enough that the end portion 10 of protruding element 7 is directed in a direction of a chord of a cross-section of the plunger rod 3. As in FIG. 2, the dimensions and materials mentioned in connection with FIG. 1 apply here as well.

FIGS. 4a and 4b disclose cross-sectional side views of the embodiment from FIG. 1 where the reciprocal movement of the engagement member 4 due to a movement of plunger rod 3 is illustrated. As can easily be understood from these figures, the drawback with a bias in a wrong direction of the engagement member known from prior art solutions is avoided with the solution of the present invention. Further, in FIGS. 4a and 4b one imaginable shape of the flanges of the grooved surface 5 is described. This is, however, only an example as many other shapes are also conceivable within the scope of the appended claims.

FIG. 5 shows a perspective view of a syringe according to an embodiment of the present invention. Here, the retention of the engagement member 4 (not shown) is achieved by means of a cap 5. As described earlier, this retention can be done in many other manners as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope of the claims.

The injection of botulinum toxin has been mentioned as a possible area of use for the device according to the invention. Naturally, it is possible to use the device according to the present invention with other liquid compositions, and gel compositions, such as hydrogels. The device is also useful for injecting cross linked or non-cross linked hyaluronic acid gels and other types of dermal fillers than hyaluronic acid, e.g. collagen, calcium hydroxyl apatite, poly-L-lactic acid (PLLA), other polysaccharides and polymethylmethacrylate (PMMA). Furthermore, the device is useful for injecting liquid compositions comprising active substances and/or bioactive agents, such as local anesthetics, cicatrizants, antioxidants, insulin or growth hormones. One preferred liquid composition of this type is a gel composition with a hyaluronic acid gel carrier and an active substance and/or a bioactive agent, e.g. a local anesthetic or a cicatrizant, such as dextranomer beads.

The invention claimed is:

1. A syringe, comprising:
a barrel,
a plunger moveably arranged within said barrel,
a plunger rod for driving said plunger, and
an engagement member arranged at the barrel to engage with grooves disposed on a surface of a circumferential portion of the plunger rod so as to provide feedback to a user as the plunger rod is moved relative to the barrel for driving said plunger,
wherein said barrel and said engagement member are arranged relative to each other such that the engagement member, due to the engagement with the grooves of the plunger rod, is movable solely in a direction generally perpendicular to a longitudinal direction of said plunger rod as the plunger rod is moved relative to the barrel,
wherein the grooves are provided continuously on the surface of the circumferential portion of the plunger rod, the grooves being defined by flanges projecting from the surface of the circumferential portion,
wherein the feedback comprises audible feedback generated when the engagement member contacts the flanges, the audible feedback being generated at regular intervals corresponding to a predetermined dose amount administered via the syringe,
wherein the engagement member comprises a main part having a circular or semi-circular shape and a protruding element protruding from said main part for engaging the grooves of the plunger rod,
wherein said protruding element is connected to the main part along an edge of the protruding element, said edge extending generally in parallel with the longitudinal direction of the plunger rod, and
wherein the protruding element is formed by folding a portion of the main part of the engagement member from a remainder of the main part along said edge.

2. The syringe according to claim 1, wherein the engagement member is arranged within the barrel.

3. The syringe according to claim 1, wherein the engagement member is arranged at the barrel immovable in a direction parallel to the longitudinal direction of the plunger rod.

4. The syringe according to claim 1, wherein:
the engagement member is a semi-circular component arranged in a compartment of the barrel, which is generally shaped as an annulus;
the plunger rod extends through the inner circle of the annulus; and
the engagement member is structured to engage the grooves of the plunger rod through an opening in the compartment.

5. The syringe according to claim 1, wherein an end portion of the engagement member engaging with the grooves of the plunger rod is tapered so as to provide feedback to the user irrespective of a direction of movement of the plunger rod.

6. The syringe of claim 1, further comprising an adjustment tab operable to cause cessation of the audible feedback.

7. The syringe according to claim 3, wherein the immovable arrangement of the engagement member at the barrel is achieved by a press fit between the engagement member and the barrel.

8. The syringe according to claim 3, wherein the immovable arrangement of the engagement member at the barrel is achieved by a snap lock.

9. The syringe according to claim 3, wherein the immovable arrangement of the engagement member at the barrel is achieved by a cap arranged at the barrel.

10. A syringe, comprising:
a barrel,
a plunger moveably arranged within said barrel,
a plunger rod for driving said plunger, and
an engagement member arranged at the barrel to engage with grooves disposed on a surface of a circumferential portion of the plunger rod so as to provide feedback to a user as the plunger rod is moved relative to the barrel for driving said plunger,
wherein said barrel and said engagement member are arranged relative to each other such that the engagement member, due to the engagement with the grooves of the plunger rod, is movable solely in a direction generally perpendicular to a longitudinal direction of said plunger rod as the plunger rod is moved relative to the barrel,
wherein the grooves are provided continuously on the surface of the circumferential portion of the plunger rod, the grooves being defined by flanges projecting from the surface of the circumferential portion,
wherein the feedback comprises audible feedback generated when the engagement member contacts the flanges, the audible feedback being generated at regular intervals corresponding to a predetermined dose amount administered via the syringe,
wherein the engagement member comprises a main part having a circular or semi-circular shape and a protruding element protruding from said main part for engaging the grooves of the plunger rod, and
wherein said protruding element is formed by punching a portion of the main part of the engagement member from a remainder of the main part.

11. A syringe, comprising:
a barrel,
a plunger moveably arranged within said barrel,
a plunger rod for driving said plunger, and
an engagement member arranged at the barrel to engage with grooves disposed on a surface of a circumferential portion of the plunger rod so as to provide feedback to a user as the plunger rod is moved relative to the barrel for driving said plunger,
wherein said barrel and said engagement member are arranged relative to each other such that the engagement member, due to the engagement with the grooves of the plunger rod, is movable solely in a direction generally perpendicular to a longitudinal direction of said plunger rod as the plunger rod is moved relative to the barrel, and
wherein the grooves are provided continuously on the surface of the circumferential portion of the plunger rod, the grooves being defined by flanges projecting from the surface of the circumferential portion,
wherein the engagement member comprises:
a semi-circular portion having a first lateral side and a second lateral side, wherein
the first lateral side has a height that is a maximal height of the engagement member, and the second lateral side tapers to an end portion that is a minimum height of the engagement member, and
a protrusion formed at the end portion and opposed to the first lateral side,
wherein the first lateral side and the second lateral side are formed at opposite ends of the engagement member and are opposed to each other in a direction of movement of the engagement member.

12. The syringe according to claim 11, wherein the protruding element is arranged as an extension of the main part and has a narrower bending radius than said main part such that an end portion of the protruding element engages the grooves of the plunger rod.

\* \* \* \* \*